United States Patent [19]
Campo et al.

[11] Patent Number: 6,020,309
[45] Date of Patent: Feb. 1, 2000

[54] PHARMACEUTICALS BASED ON PAPILLOMAVIRUSES

[75] Inventors: Maria Saveria Campo; William Fleming Hoggan Jarrett, both of Glasgow, United Kingdom

[73] Assignee: Cancer Research Campaign Technology Limited, London, United Kingdom

[21] Appl. No.: 08/525,764

[22] PCT Filed: Mar. 31, 1994

[86] PCT No.: PCT/GB94/00683

§ 371 Date: Jan. 24, 1996

§ 102(e) Date: Jan. 24, 1996

[87] PCT Pub. No.: WO94/23037

PCT Pub. Date: Oct. 13, 1994

[30] Foreign Application Priority Data

Mar. 31, 1993 [GB] United Kingdom .................. 9306731

[51] Int. Cl.[7] ........................... A61K 38/04; A61K 38/16
[52] U.S. Cl. ................................... 514/12; 514/2; 514/8; 514/13; 514/14; 514/15; 514/16; 514/17; 514/18; 514/19; 424/192.1; 424/186.1
[58] Field of Search .............................. 514/2, 8, 12, 13, 514/14, 15, 16, 17, 18, 19; 424/192.1, 156.1, 184.1; 435/69.1, 69.7, 172.3; 530/403

[56] References Cited

FOREIGN PATENT DOCUMENTS

| | | |
|---|---|---|
| 0133123 | 7/1984 | European Pat. Off. . |
| 0344940 | 5/1989 | European Pat. Off. . |
| 0375555 | 12/1989 | European Pat. Off. . |
| 92-05248 | 4/1992 | WIPO . |
| 93-00436 | 1/1993 | WIPO . |
| 93-02184 | 2/1993 | WIPO . |
| 93 20844 | 10/1993 | WIPO . |

OTHER PUBLICATIONS

Stedman. Stedman's Medical Dictionary, 24th ed., Williams and Williams, Baltimore, p. 1148, 1982.
Jarrett et al. Virology 184:33–42, 1991.
Christensen et al. Virology 181:572–579, 1991.
Lin et al. Virology 187:612–619, 1992.
"Immunostimulation" (Chedid et al., eds.) Springer–Verlag: Berlin, Heidelberg, New York (1980) pp. 5–22.
Mosmann et al., "The role of IL–10 in crossregulation of $T_h1$ and $T_h2$ responses," *Immunology Today*, 12(2):A49–A53 (1991).
British Pharmacopoeia 1998, vol. II:1047 (1998).

*Primary Examiner*—Elizabeth Kemmerer
*Attorney, Agent, or Firm*—Klarquist Sparkman Campbell Leigh & Whinston, LLP

[57] ABSTRACT

The invention provides pharmaceutical formulations for Immunizing against papillomavirus tumors or lesions. Formulations may be selected from the group consisting of: (i) a formulation which comprises a papillomavirus (PV) L2 protein or fragment thereof that is effective to provide a protective effect to lessen the occurrence and severity of lesions or tumors caused by PV infection and an aluminum compound; (ii) a formulation which comprises a bovine papillomavirus (BPV) L2 protein or said fragment thereof and an aluminum compound: (iii) a formulation which comprises a BPV4 L2 protein or said fragment thereof and an aluminum compound; (iv) a formulation which comprises a BPV-4 protein or said fragment thereof and an adjuvant; (v) a formulation which comprises a BPV-4 L2 protein or said fragment thereof and an adjuvant; and (vi) a formulation which comprises a BPV4 protein or said fragment thereof and an aluminum compound.

7 Claims, 3 Drawing Sheets

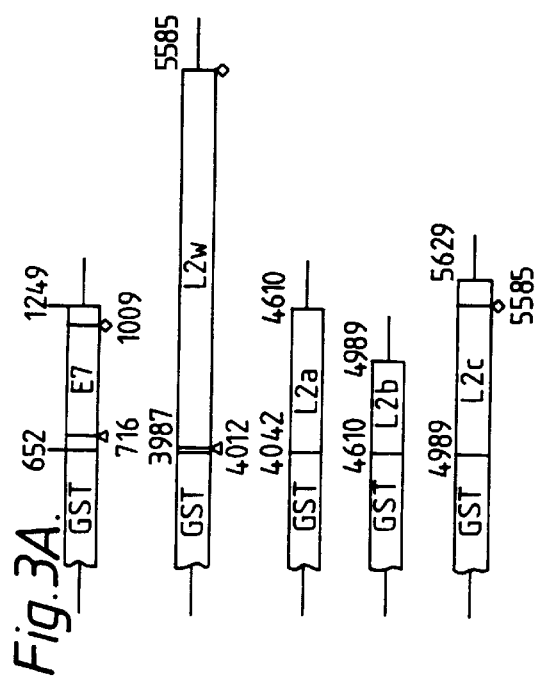

PHARMACEUTICALS BASED ON PAPILLOMAVIRUSES

SUMMARY OF THE INVENTION

The present invention relates to pharmaceuticals based on papillomaviruses.

Papillomaviruses induce a variety of lesions both in humans and in animals. Some papillomas, albeit benign, are themselves a clinical problem, such as laryngeal papillomas of children or penile papillomas of bulls and others are known to be a risk factor in the pathogenesis of cancer, as in the case of flat lesions of the cervix or penile condylomata in humans. Therefore both in human and veterinary medicine, antiviral pharmaceuticals against papillomaviruses e.g. for prophylactic use to protect against the establishment of a serious infection would be of major advantage.

Vaccination studies in humans present several problems. First of all experimentation is ethically unacceptable. Secondly, very limited amounts of virus are available as some lesions, in particular those of the cervix, do not produce viral progeny, and no in vitro system is yet available which allows vegetative replication of virus.

The production of viral proteins in bacteria and the use of synthetic peptides have circumvented this last problem and have allowed the ongoing analysis of the immune response to papillomavirus infection (see for instance Jenison et al, 1988 J. Virol, 62 p. 2115 and Tindle et al, 1990 J. Gen. Virol, 71 p. 1347.

Effective prophylactic vaccines, both natural (Jarrett et al, 1990 The Vet. Record, 126 p. 449) and genetically engineered (Pilachinski et al, 1986 Ciba Foundation Symposium Vol. 120 p. 136) have already been produced against bovine papillomaviruses, and regression of Shope papillomas has been achieved by vaccinating rabbits with tumour tissue extracts (Evans et al, 1962 J. Nat. Cancer Inst. 29 p. 277). The bovine system is an excellent model for papillomavirus induced diseases in the human and for medicaments against such diseases in humans given the several similarities between the bovine and human disease. Namely multiple virus types with high lesion specificity (Jarrett et al, 1984 Virol. 136 p. 255), homology of genetic structure, and progression of some lesions to malignancy. The bovine system also presents several advantages in that cofactors in oncogenesis are known (Campo and Jarrett, 1986 In Papillomaviruses, Ciba Foundation Symposium 120, John Wiley and Sons p. 117) and, above all, direct experimentation is possible (Jarrett, 1985 In advances in Viral Oncology (Ed. G. Klein) 5 p.83).

Vaccination has been traditionally regarded as a prophylactic measure. Hosts are immunised against a pathogen and on subsequent exposure to the same organism, the infection is aborted at a preclinical stage. This is usually accomplished in virus infections by a neutralizing event directed at a superficial epitope on a structural protein. Virus-induced tumours such as papillomas often persist for long periods and are then, in a proportion of cases, rejected. The host may then be immune to reinfection (Jarrett, 1985 supra). The nature of the rejection mechanism and its mediators is unknown, but it is advantageous to induce the rejection mechanism early in a tumour life cycle. In veterinary practice, it has been known for a long time that crude extracts of papillomas could sometimes, but by no means always, cause the rejection of homologous papillomas (Olson et al, 1959 Am. J. Vet. Res. 21 p. 233, Evans et al, 1962 supra). These experiments were carried out before it was known that there were different types of papillomavirus in a species (Jarrett et al, 1984 supra; de Villier, 1989 J. Virol. 63 p. 4898), and that these are probably all immunologically type-specific (Jarrett et al. 1990 The Vet. Record 126 p. 473; Jenison et al, 1988 supra).

Papillomaviruses can infect and cause tumours in both cutaneous and mucous epithelia. In man and animals mucosal papillomas are often serious lesions which tend to run a prolonged course, as in the case of human laryngeal, genital and cervical papillomas (Steinberg, 1987 In the Papovaviride Vol. 2 (ed. N. P. Salzman and P. M. Howley) p. 265; zur Hausen, 1991 Virol. 184 p. 9). These may be causal factors in the subsequent development of malignancies, as in the case of human papillomavirus (HPV) type 16-associated cervical carcinoma in women (zur Hausen, 1991 supra), and bovine papillomavirus (BPV) type 4-associated alimentary cancer in cattle (Campo and Jarrett, 1986 supra). Clearly, there is an urgent need for pharmaceuticals against papillomavirus diseases.

Despite recent limited success (Kreider et al, 1986 J. Virol. 59 p. 369; Sterling et al, 1990 J. Virol. 64 p. 6305; Meyers et al, 1992 Science 257 p. 971; Dollard et al, 1992 Genes and Development 6 p. 1131), papillomaviruses are notoriously refractory to growth in cultured cells (Teichaman and LaPorta, 1987 In The Papovaviridae, Vol. 2 (ed. N. P. Salzman and P. M. Howley) p. 109) and the consequent lack of viral reagents has delayed the analysis of the immune response to the infection. The recent availability of recombinant technology has allowed the production of both early and late viral proteins in large amounts and in a purified form (Tindle et al, 1990 supra.; Jarrett et al, 1991 Virol. 184 p. 33; Ghim et al, 1992 Virology 190 p. 548; Stacey et al, 1992 J. Gen. Virol. 73 p. 2337) and thus has for the first time made it possible to study their immunising potential. It has already been shown that in cattle it is possible to use viruses and tumour extracts to induce both protection against, papillomavirus-induced cutaneous lesions (Jarrett et al, The Vet Record 1990 126 p. 473; The Vet Record 1990 126 p. 449) and to use recombinant proteins to induce both protection against and rejection of PV-induced cutaneous lesions (Virology 1991, 184 p. 33). The applicants now show that one can vaccinate in a practically significant fashion against papillomavirus for example the mucosal virus BPV-4, which in the field is a causative factor of squamous cell carcinoma of the upper alimentary canal (Campo and Jarrett, 1986 supra).

The present invention provides a pharmaceutical formulation for the prophylaxis of papillomavirus tumours or lesions selected from the group consisting of: (i) a formulation which comprises a papillomavirus (PV) L2 protein or prophylactically effective fragment thereof and an aluminium compound, (ii) a formulation which comprises a bovine papillomavirus (BPV) L2 protein or prophylactically effective fragment thereof and an aluminium compound; (iii) a formulation which comprises a BPV-4 L2 protein or prophylactically effective fragment thereof and an aluminium compound; (iv) a formulation which comprises a BPV-4 protein or prophylactically effective fragment thereof and an adjuvant; (v) a formulation which comprises a BPV-4 L2 protein or prophylactically effective fragment thereof and an adjuvant; (vi) a formulation which comprises a BPV-4 protein or prophylactically effective fragment thereof and an aluminium compound; (vii) a formulation which comprises a PV L2 protein or prophylactically effective fragment thereof and an adjuvant; (viii) a formulation which comprises an HPV L2 protein or a prophylactically effective fragment thereof and an adjuvant; (ix) a formulation which comprises an HPV L2 protein or a prophylactically effective fragment thereof and an aluminium compound; (x) a formulation which comprises an HPV-16 L2 protein or a prophylactically effective fragment thereof and ad adjuvant; (xi) a formulation which comprises an HPV-16 L2 protein or a prophylactically effective fragment thereof and an aluminium compound.

The pharmaceutical formulation may comprise a PV L2 protein or a prophylactically effective fragment thereof and an aluminium compound. The PV may be BPV. The BPV may be BPV-4.

The papillomavirus protein or prophylactically effective fragment thereof may be in the form of a fusion protein with a different co-protein. The co-protein may be glutathione-S-transferase.

The papillomavirus protein or prophylactically effective fragment thereof may be produced by recombinant DNA techniques.

The aluminium compound may comprise a mixture of aluminium hydroxide and aluminium phosphate. There may be 3% aluminium hydroxide and 2% aluminium phosphate. The aluminium compound may be aluminium gel.

Also provided is the use of a pharmaceutical formulation as above in medicine for the prophylaxis of papillomavirus tumours or lesions.

Also provided is use of (i) a PV L2 protein or prophylactically effective fragment thereof and an aluminium compound; or (ii) a BPV L2 protein or prophylactically effective fragment thereof and an aluminium compound; or (iii) a BPV-4 L2 protein or prophylactically effective fragment thereof and an aluminium compound; or (iv) a BPV-4 protein or prophylactically effective fragment thereof and an adjuvant; or (v) a BPV-4 L2 protein or prophylactically effective fragment thereof and an adjuvant; or (vi) a BPV-4 protein or prophylactically effective fragment thereof and an aluminium compound; or (vii) a PV L2 protein or prophylactically effective fragment thereof and an adjuvant; or (viii) an HPV L2 protein or a prophylactically effective fragment thereof and an adjuvant; or (ix) an HPV L2 protein or a prophylactically effective fragment thereof and an aluminium compound; or (x) an HPV-16 L2 protein or a prophylactically effective fragment thereof and all adjuvant; or (xi) an HPV-16 L2 protein or a prophylactically effective fragment thereof and an aluminium compound in the production of a vaccine for the prophylaxis of papillomavirus tumours or lesions.

Also provided is a method of immunising a mammal against papillomavirus tumours or lesions which comprises the administration of a pharmaceutical formulation as above in a therapeutically effective dosage.

Vaccines based upon the pharmaceutical formulations for prophylactic use as described above, can be prepared in accordance with methods well known in the art. Likewise, dosage rates can be determined according to known methods. Attention is directed to New Trends and Developments in Vaccines, Editors A. Voller and H. Friedman, University Park Press, Bultimore, 1978 and to Remington's Pharmaceutical Science by E. W. Martin.

In order that the invention is more clearly understood, it will be further described by way of example only, and not by way of limitation, with reference to the following figures.

BRIEF DESCRIPTION OF THE DRAWINGS

FIGS. 3A–D shows results for vaccination with E7+L2 and L2. A, pGEX recombinant plasmids. B–D, number of tumours in calves eleven weeks after challenge; B, group 1 (E7+L2 vaccine); C, group 2 (L2 vaccine); D, group 3 (control).

DETAILED DESCRIPTION OF THE INVENTION

Materials and Methods

Figure 1B:
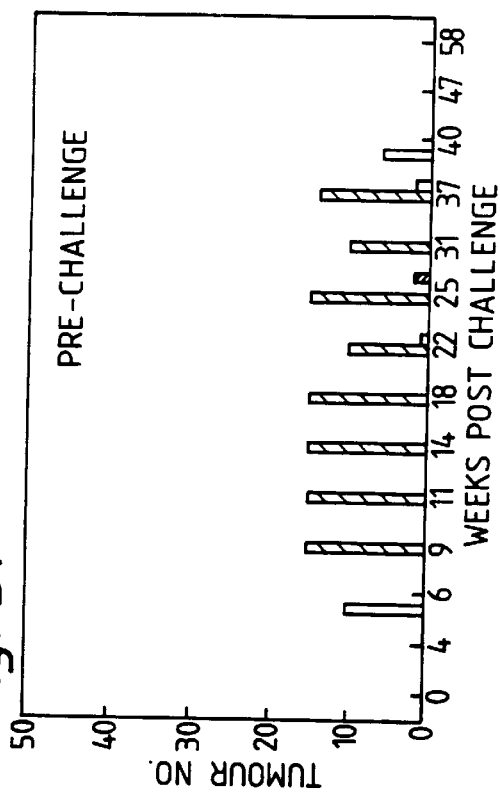
FIGS. 1A–D shows results for vaccination with β-gal-early (E1, E2, E4 and E7) fusion proteins. A, animal No. 132 from group 3 (control. B, animal No. 146 from group 1 (pre-challenge vaccination). C, animal No. 139 from group 2 (post-challenge vaccination). Bar legend is in FIG. D, pURE7. The recombinant plasmids containing E1, E2 and E4 ORFs are not shown.
Figure 1D:
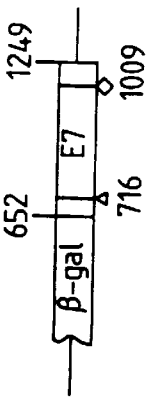

All genetic manipulation procedures are carried out according to standard methods described in "Molecular Cloning", A Laboratory Manual eds. Sambrook, Fritsch and Maniatis, Cold Spring Harbor Laboratory Press, 1989.

In the following it is described how the applicants produced recombinant BPV-4 peptides in *Escherichia coli* using pAT153 as a source of E7 and L2. Alternatively the invention may be put into effect by use of the L2 and E7 sequence information available from EMBL sequence database (accession no. X59063).

Calves

Calves of mixed breed, approximately 12 weeks old, were obtained from papilloma-free sources. They were randomly assigned to groups and housed in separate, clean, well-ventilated pens in an isolation unit. All the calves were bled on arrival and at three to four weeks intervals thereafter for haematological analysis. The animals were cared for in complete accordance with the directives of the Home Office of Great Britain.

Production of recombinant BPV-4 peptides in *Escherichia coli*

(i) β-Galactosidase E7 Fusion Proteins

The E1, E2, E4 and E7 open reading frames (ORFs) of BPV-4 were cloned in the pUR plasmid series (Ruther and Muller-Hill, 1983 EMBO J. 2 p. 1791). The cloning of the E1, E2 and E4 ORFs is not described.

The ORF encoding the E7 peptide was isolated by digesting the BPV-4 genome cloned in pAT153 (Campo M. S. et al, 1982 J. Gen. Virol. 63, p. 255) with BAMHI. The ORF encoding the E7 peptide was isolated as a BsrI fragment encompassing nucleotides (nts) 652–1249 and cloned in pUR 278 (Ruther and Mullter-Hill 1983 supra) via addition of BamHI linkers. The recombinant plasmid was transfected. into *Escherichia coli* JM109 (Promega Ltd, Southampton, UK). The bacteria were grown to mid-log phase in L-broth supplemented with 100 µg/ml ampicillin and induced to express the β-gal-fusion protein by addition of 100 µg/ml IPTG for 1–4hr. β-gal-E7 was prepared by suspending bacteria in lysozyme buffer (25% sucrose, 10 mM $MgCl_2$, 50 mM Tris HCl pH 8.0, 1 mg/ml lysozyme) containing 300 µg/ml DNase I. The fusion peptide was pelleted following cell lysis in 0.25% NP40, 0.125% deozycholate, 0.25 M NaCl, Tris HCl pH 7.2 and subsequent washes in 1.75 M Guanidine HCl, 1 M NaCl, 1% Triton X100.

(ii) Glutathione-S-transferase (GST) Fusion Proteins

The E7 and L2 ORFs were cloned in pGEX (Smith and Johnson, 1988 Gene, 67 p. 31).

The ORF encoding the E7 peptide was isolated as described above and cloned in pGEX 3X (Pharmacia Ltd, Milton Keynes MK9 3HP, UK) by blunt-end ligation (see FIG. 3).

The ORF encoding the L2 peptide isolated by digesting the BPV-4 genome cloned in pAT 153 (Campo et al 1982 supra) was obtained as a BamHI-EcoRI fragment encompassing nt 3987–5585 and cloned in its entirety in pGEX 2T (Pharmacia Ltd, Milton Keynes MK9 3HP, UK), and also as three Dde I fragments: (i) a 5' end fragment (nt 4042–4610) in pGEX 2T; (ii) a middle fragment (nt 4610–4989) in PGEX 3X; and (iii) a 3' end fragment (nt 4989–5629) in pGEX 3X (see FIG. 3). The GST fusion peptides represent the E7 protein from amino acids −21 to 98 (GST-E7); the L2 protein from amino acids −8 to 542 (GST-L2w) amino acids 11–200 (GST-L2a); amino acids 201–326 (GST-L2b); and amino acids 327–542 (GST-L2c). Transformation and growth of bacteria and production of GST-fusion peptides were carried out as outlined for β-gal E7. The peptides were prepared in bulk by pelleting inclusion bodies from bacteria suspended in lysozyme buffer containing DNase I at 300 μg/ml and deoxycholate at 1 mg/ml, followed by washing in 0.5% Triton X100/10 mM EDTA, pH 8.0. In all cases fusion peptides were suspended by boiling and sonication in 5% SDS, 5 mM B-Mercaptoethanol, 50 mM Tris HCl, pH 8.0 prior to vaccination. Yields were 2–3 mg per gram wet weight of bacteria and 50–70% purity was routinely achieved.

Characterization of fusion proteins

The β-gal-E7, GST-E7 and GST-L2 peptides were characterised by SDS-PAGE electrophoresis. The molecular weights of the fusion peptides were all in agreement with prediction. β-gal-E7 and GST-E7 were characterised immunologically using rabbit, bovine or murine antisera raised against β-gal-E7 or GST-E7 or GST-E7, in ELISA or Western blot analysis following absorption with the appropriate bacterial protein. The immune sera reacted positively with both the homologous and the heterologous antigen, showing that the fusion proteins were immunologically active and the sera were specific for E7 (see Table 1). GST-L2 antigens were reactive in ELISA tests with homologous bovine sera, as was a β-gal L2 fusion protein, showing that GST-L2 was active immunologically and the sera were specific for L2 (see Table 1).

Experimental design (i) Vaccination with E1, E2, E4, E7 early fusion proteins

Eighteen animals were divided into three groups of six animals each. Each animal in group 1 was inoculated in the posterior left flank with 1 ml of PBS containing 1 mg of a cocktail of β-gal-early (E1, E2, E4 and E7) fusion proteins emulsified in 1 ml of Freund's incomplete adjuvant (FIA); vaccination (boost) was repeated with a fortnight in the posterior right flank. Two weeks after the boost, all of the animals in each group were challenged in the palate (Jarrett et al, 1990 The Vet Record, 126 p. 473) with 1012 particles of BPV-4. Animals in group 2 were vaccinated as above two weeks after challenge, and boosted after a further two weeks. BPV-4 was purified from oesophageal papillomas and typed as described previously (Campo et al, 1980 Nature, 286, p. 180) and the concentration of viral particles was estimated by the electron microscope assay (Jarrett et al, 1990 The Vet Record, 126 p. 449). Each animal was examined every three to four weeks, the papillomas were counted and their size measured as previously described (Jarrett, 1985 supra).

(ii) Vaccination with β-gal-E7

Nineteen animals were divided into two groups of eleven and eight animals each. The eleven calves in group 1 were each given a 1 mg/1 ml suspension of the β-gal-E7 fusion protein emulsified in 1 ml of FIA into the right quadriceps muscle. The vaccination was repeated four weeks later into the left quadriceps muscle (boost). Fourteen days after the boost, all the animals in group 1 and 2 were challenged in the palate with $10^{11}$ BPV-4 particles at ten sites ($10^{10}$ particles per site). The animals were examined and the papillomas monitored as above.

(iii) Vaccination with GST-E7 and GST-L2

Forty-seven animals were divided into two groups of fifteen animals each (group 1 and 2) and one group of seventeen animals (group 3). The calves of group 1 were each given a 2 ml suspension containing 1 mg of the GST-E7 fusion protein and 1 mg in total of the GST-L2 fusion peptides (the ratio of the GST-fusion peptides L2w:L2a:L2b:L2c was approximately 1:5:5:5) plus 2 ml of FIA into the right quadriceps muscle. The vaccination was repeated four weeks later into the left quadriceps muscle. The calves of group 2 were each given 1 mg of the GST-L2 fusion proteins as described above. Two weeks after the boost the animals in all three groups were inoculated in the palate at ten different places with a total of $10^{11}$ BPV-4 particles ($10^{10}$ particles per site). The animals were examined and the papillomas monitored as above.

TABLE 1

FUSION PROTEINS ARE IMMUNOLOGICALLY ACTIVE

|  |  | blank | no Ag | no Ab | β-gal |  | GST |  |
|---|---|---|---|---|---|---|---|---|
|  |  |  |  |  |  | β-gal:E7 |  | GST-E7 |
| Animal 5 | pre-Immune | 0.064 | 0.104 | 0.105 | 0.153 | 0.206 | 0.132 | 0.134 |
| (β-gal-E7) | Immune | 0.058 | 0.192 | 0.174 | 0.718 | <u>2.892</u> | 0.112 | <u>0.886</u> |
|  |  |  |  |  |  | β-gal-L2 |  | GST-L2 |
| Animal 16 | pre-Immune | 0.064 | 0.149 | 0.124 | 0.15 | 0.231 | 0.284 | 0.317 |
| (GST-L2) | Immune | 0.087 | 0.157 | 0.105 | 0.12 | <u>1.512</u> | 0.724 | <u>2.694</u> |

Microtitre wells were coated with 500 μg/well of E7 fusion protein or 100 μg/well of L2 fusion protein. β-gal and GST were used in equivalent amounts. The wells were incubated overnight with the appropriate bovine sera and anti bovine IgG conjugated with Alkaline Phosphatase was added for 1 hour. Animal 5 is from exp 3, group 1; animal 16 is from exp 4, group 2.

(iv) Vaccination with GST-L2 in aluminium gel

Thirty-six animals were divided into three groups of twelve animals each. The calves of group 1 were each given a 3 ml suspension containing 1 ml of GST-L2 fusion peptides at 1 mg/ml in the same ratio as above, 1 ml of 40 mM TRIS-HCl-0.33% NaCl, and 1 ml of aluminium gel, made up of equal volumes of 3% aluminium hydroxide and 2% aluminium phosphate (Intervet UK Ltd, Cambridge Science Park, Cambridge CB4, UK). The vaccination was repeated four weeks later. The calves of group 2 were vaccinated as above, but with only 100 µg of L2 fusion peptides per animal. The calves of group 3 were the control. The challenge was as above.

Results

Immunization with the E7 protein inhibits papilloma development and causes papilloma rejection E7 is the major transforming protein of BPV-4 in vitro (Jagger et al, J. Gen. Virol. 71 p. 3041) and is expressed throughout the different development stages of alimentary canal papillomas, pointing to its importance for the maintenance of the proliferative state also in vivo. It is homologous to the oncoprotein E7 of human papillomavirus type 16 (HPV-16) (Jagger et al, 1990 supra; Jackson et al, 1991 Molecular Carcinogenesis 4 pg. 382), the virus most often associated with squamouse cell carcinoma of the uterine cervix in women (zur Hausen, 1991 supra). Because of its pivotal role in cell transformation, E7 may be a target for cell-mediated immune responses leading to tumour rejection, both in BPV-4 and in HPV-16.

The applicants conducted two pilot experiments, which will be described briefly, and a third experiment with larger numbers of animals, which will be described in more depth.

In the first experiment, the applicants vaccinated calves with a cocktail of BPV-4 early proteins E1, E2, E4 and E7, synthesized in bacteria as β-galactosidase fusion products (Ruther and Muller-Hill 1983 supra; Jarrett et al, 1991 Virol., 184 p. 33). Six calves in group 1 were vaccinated before being challenged in the mouth with BPV-4, and six calves in group 2 were vaccinated after challenge. Six control calves in group 3 were not vaccinated and were challenged with BPV-4 (see Table 2). Four to six weeks after challenge, all the animals developed plaque-like lesions, which are stage 1a of alimentary canal papilloma development (Jarrett, 1985 supra). The lesions were confined to the injection sites. During the next twenty weeks, the lesions of the control animals grew in number and size, with secondary spread in the palate; and went through the well recognised stages of papilloma growth: raised plaques (stage 1b), papillomas up to 2 mm in length (stage 2) and papillomas bigger than 2 mm (stage 3). Stage 2 and stage 3 papillomas are the mature virus-producing tumours.

TABLE 2

VACCINATION STRATEGY

| Group | Exp 1 | Exp 2 | Exp 3 | Exp 4 | Exp 5 |
|---|---|---|---|---|---|
| 1 | (PR) E1-2-4-7 (6) | E7 (6) | E7 (11) | E7 + L2 (15) | L2* (12) |
| 2 | (PS) E1-2-4-7 (6) | E2 (6) | nv (8) | L2 (15) | L2** (12) |
| 3 | nv (6) | nv | | nv (17) | nv (12) |

The number of animals in each group is in parentheses. The animals were inoculated twice with 1 mg of protein, except in exp 5, group 2 where they received two inoculations of 100 µg each (L2**). The adjuvant was FIA in all cases, except in exp 5 (L2* and L2**) were it was aluminium gel (Intervet UK, Ltd). In exp 1, PR indicates vaccine given pre-challenge and PS indicates vaccine given post-challenge; in exp 2–5, the vaccine was always administered pre-challenge nv. no vaccine.

Figure 1A:
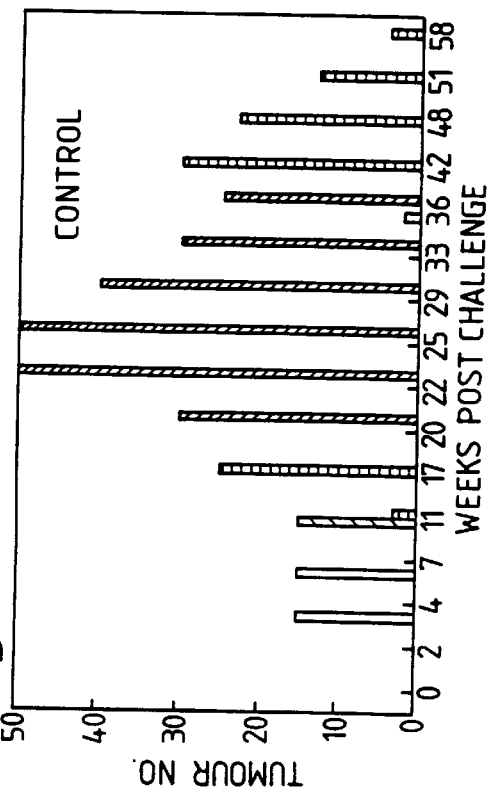
Figure 1C:
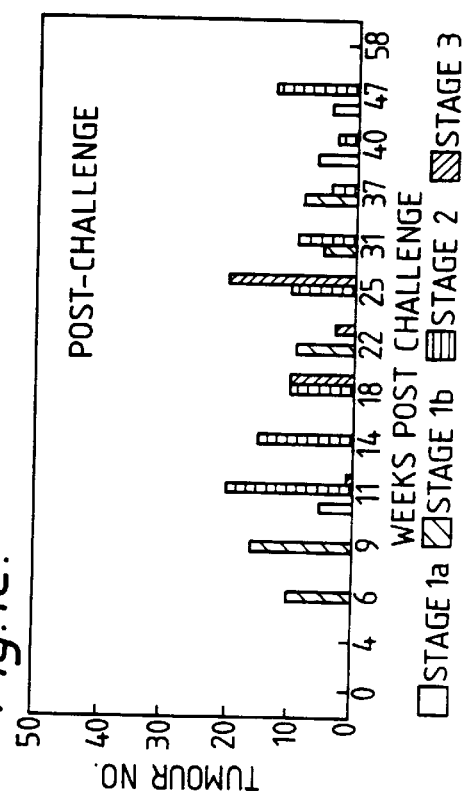

Details of the papilloma developmental stages and their significance in the tumour life cycle have been described (Jarrett, 1985 supra). Approximately thirty weeks after challenge, natural involution of papillomas started to take place with decrease in size and number of lesions, and the animals were essentially papillomatosis-free by week fifty-four. The development of papillomas in a representative animal from this group is shown in FIG. 1A. All the vaccinated animals, whether vaccinated before or after challenge, had approximately the same number of plaques as the control animals, indicating that the virus was equally infectious and the calves equally susceptible to infection in the three groups. However most of the lesions in the vaccinated animals did not develop to full size, particularly in group 1, and were most rejected by 40–47 weeks after challenge, much earlier than in the control animals. The development of lesions in representative animals from the vaccinated groups are shown in FIGS. 1B and C. Two conclusions could be drawn from these results: that therapeutic vaccination was possible, and that, within the time intervals used in this study, the time of vaccination relative to challenge was not critical.

To ascertain which one of the four early proteins was responsible for tumour regression, the applicants vaccinated six calves with β-gal-E7 and six with β-gal-E2 before challenge; six animals were the control group (see Table 2). The E2-vaccinated animals did not behave any differently from the control group, while in the E7-vaccinated calves most of the lesions did not grow beyond stage 1a and were rejected earlier than either in the control or in the E2-vaccinated animals (data not shown).

Figure 2B:
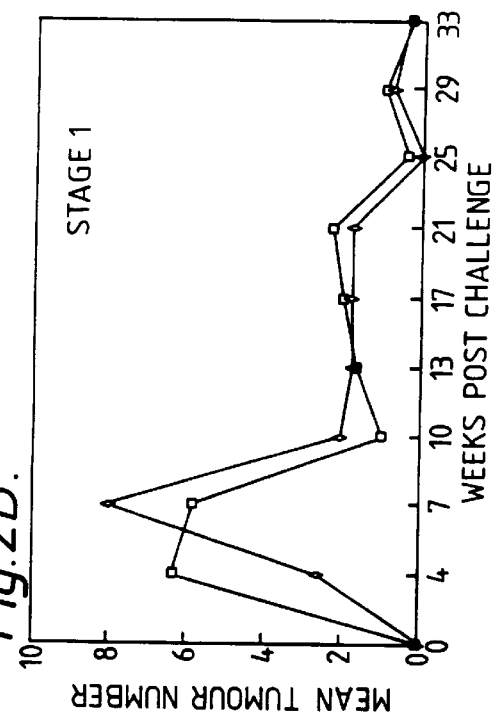
FIGS. 2A–D shows results for vaccination with β-gal-E7. A, mean number of all tumours in vaccinated and control animals. B, mean number of stage 1 tumours. C, mean number of stage 2 tumours. D, mean number of stage 3 tumours. Squares, vaccinated animals; diamonds, control animals. In a repeated measurement analysis, P=0.02 in C and 0.04 in D.
Figure 2D:
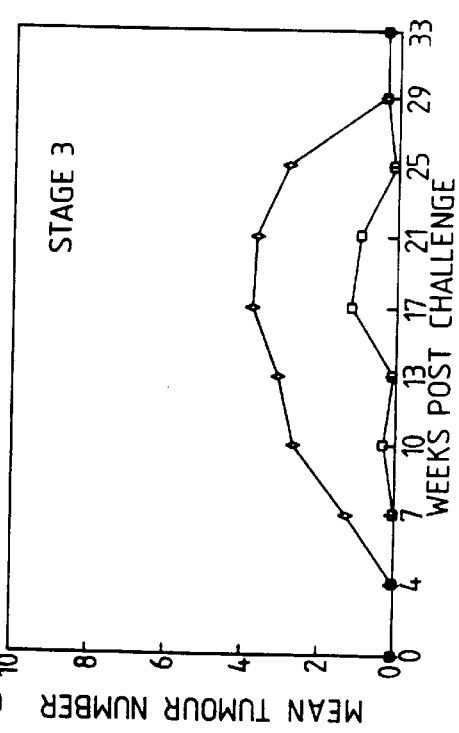
Figure 2A:
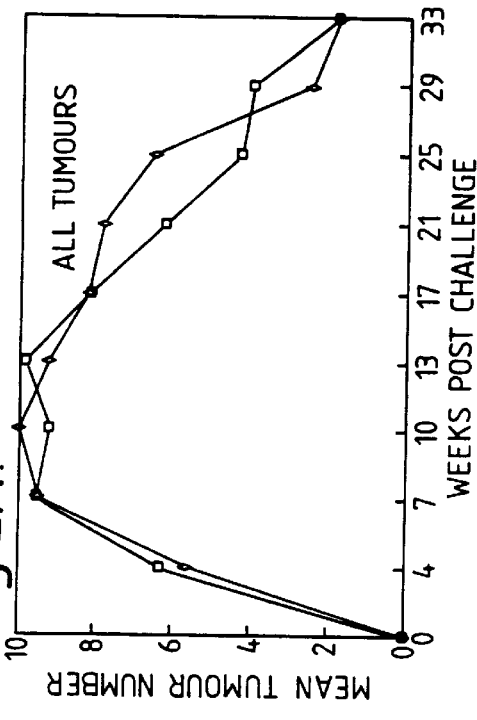
Figure 2C:
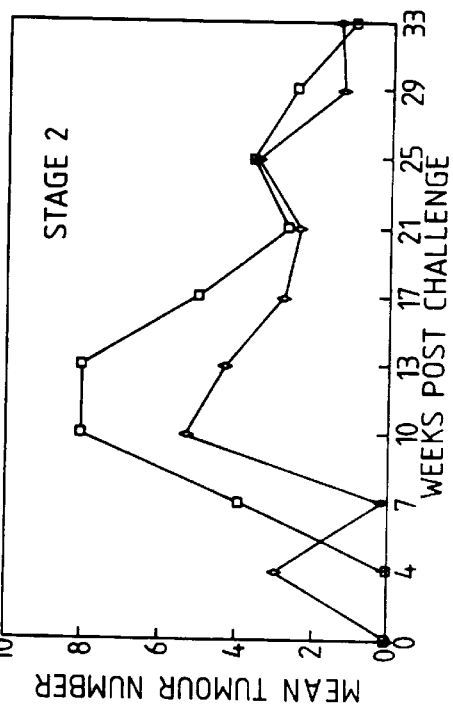

In the third larger experiment, eleven calves were vaccinated with β-gal-E7 before challenge and eight calves were kept as controls (see Table 2). In this experiment plaques and raised plaques will be considered together as stage 1 lesions. As previously, all the animals developed the same number of plaques four weeks after challenge, confirming that they were all equally susceptible to infection (see FIG. 2A). After ten weeks, the number of stage 1 lesions fell sharply in both groups, concomitant with the increase in the number of stage 2 lesions (see FIGS. 2B and C). In the control group, the stage 2 lesions progressed to stage 3 lesions in the following ten weeks (see FIG. 2D) while the number of stage 1 lesions remained constant (see FIG. 2B). There was no secondary spread, due to the smaller does of challenge virus (see Materials and Methods). After five more weeks (twenty-five weeks post challenge), stage 3 and stage 2 papillomas started regressing (see FIGS. 2C and D). In the E7-vaccinated group, by week 10 after infection, the number of stage 2 lesions was higher and the number of stage 3 lesions lower than in the control group (see FIGS. 2C and D). Thirteen weeks post infection, the number of stage 2 papillomas decreased considerably, without concomitant increase in stage 3 papillomas (see FIGS. 2C and D). In the E7-vaccinated animals therefore, progression from stage 2 to stage 3 lesions was being dramatically reduced and stage 2 papillomas were regressing before reaching full maturity. The difference between the control and the vaccine group was observed not only when the number of stage 2 and stage 3 papillomas per group were considered, as in FIG. 2, but also when the percentage of stage 3 papillomas or the percentage of animals with stage 3 papillomas was considered (see Table 3).

In the three different experiments, a total of twenty-nine animals was vaccinated with E7. Twenty-two (76%) either did not develop mature papillomas or rejected them earlier than the control animals. It may therefore be concluded that vaccination with E7 reduces tumour growth and induces premature tumour regression thus effectively providing a treatment for papillomas.

Vaccine E7 is effectively presented to the immune system

Vaccination with E7 is accompanied by both a humoral and a cellular immune response to the vaccine. Both responses appear much earlier and have a greater amplitude in the vaccinated animals than in the control calves.

Whereas all of the vaccinated animals had serum antibodies to E7, serum antibodies to E7 were not in all of the control animals and some remained negative throughout the course of the experiment. Vaccine E7 is therefore presented to both effector arms of the immune system, while viral E7 is poorly presented. This may explain the efficacy of the therapeutic vaccine. The humoral and cell-mediated immune response to E7 and the mapping of the B- and T-cell epitopes will be presented in greater detail elsewhere.

Immunisation with the L2 protein prevents papilloma formation

L2 is the minor capsid protein of papillomavirus. Although the detailed molecular structure of the virion is not yet known, there is circumstantial evidence that a domain(s) of the protein is exposed on the surface of the virus (low titer virus-neutralizing L2 antibodies have been found in rabbits immunised with recombinant L2 protein (Christensen et al, 1991 Virology 181 p. 572; Lin et al, 1992 Virology 187 p. 612)). The applicants have shown that vaccination with the L2 protein of the cutaneous papillomavirus BPV-2 induced early rejection of fibropapillomas of the skin, accompanied by infiltrates of immune cells in the regressing warts (Jarrett et al, 1991 Virology 184 p. 33).

L2 and E7 were produced in bacteria as glutathione-S-transferase (GST) fusion proteins (Smith and Johnson, 1988 supra). Fifteen animals were vaccinated with GST-L2, fifteen with GST-L2+GST-E7, and seventeen were kept as control (see Table 2). All of the animals were challenged with equal amounts of virus from the same stock. The animals were examined four, seven and eleven weeks after challenge. In group 3, which had received no vaccine, 13 out of 17 calves developed lesions approximately four weeks after virus infection. These developed through the usual stages (see Table 4). Eleven weeks after challenge, when the experiment was terminated, one of the four animals that were free of lesions at four weeks had only one stage 1 lesion and three had no lesions at all (see Table 4 and FIG. 3). Of the fifteen animals in group 1 (L2+E7), two developed stage 1 lesions which subsequently disappeared, one developed stage 2 lesions, which were still present at the end of the experiment, and twelve did not develop any tumours at all (see Table 4 and FIG. 3). In group 2 (L2) by the end of the experiment one calf had five stage 1 and one stage 2 lesions, and the remaining fourteen animals were completely tumour-free (see Table 4 and FIG. 3). The 28 vaccinated animals with no tumours were still papilloma-free forty-four weeks after challenge, whereas the control animals still had papillomas. Thus the L2 and L2+E7 vaccines conferred a high degree of protection, an effect almost certainly due to the L2 protein, as the E7 vaccine has no protective effect by itself (see above). This was confirmed by a second L2 vaccination experiment, in which only the L2 peptides were used, the amount of antigen was decreased to 100 $\mu$g per inoculation per animal and the adjuvant was changed to aluminium gel (see Table 2). Most animals in group 1 (11 out of 12) and all the animals in group 2 (12 out of 12) were completely protected from challenge and tumour-free, whereas 11 out of 12 control animals developed papillomas four weeks after challenge (data not shown). The L2 peptides therefore provide a powerful prophylactic vaccine. The results show that it is possible to reduce the dosage of L2 when administered in aluminium salts, while maintaining a strong prophylactic effect.

Thus the applicants have successfully achieved prophylactic and therapeutic immunisation against mucosal bovine papillomaviruses.

This has been accomplished in an animal host against its own natural pathogen. Cattle and their papillomaviruses have co-evolved and the immunological response observed in experimental conditions mimics the one observed in nature and is therefore biologically significant (Jarrett et al, 1991 Virology, 184 p. 33; Campo, 1991 Cancer Cells, 3, p. 421).

The success obtained against the mucosal virus BPV-4 in the face of heavy challenge is particularly remarkable and of special relevance to the possible use of vaccines against genital papillomavirus in human subjects. There are several similarities between the BPV-4 and the HPV-16 systems. Both viruses infect mucous epithelia, giving rise to lesions that can neoplastically transform. In both viruses the major transforming functions, as defined in in vitro systems, are encoded by the E7 gene. Furthermore, the two E7 proteins show amino acid homology.

Virtually complete protection against BPV-4 infection was achieved by immunisation with the L2 protein. Vaccination with the L2 protein of the cottontail rabbit papillomavirus (CRPV) has also been shown to have protective effect in the rabbit (Christensen et al, 1991 supra; Lin et al, 1992 supra), although to a more limited extent than in cattle. Taken together, these two sets of results suggest that L2 of HPV might have a similar effect in humans.

Immunisation with BPV-4 E7 induces rejection of established tumours which is accompanied by a strong cellular immune response. Vaccination of rats and mice with the HPV-16 E7 gene caused growth retardation and partial regression of tumours induced by HPV-16 transformed cells (Meneguzzi et al, 1991 Virology 191 P. 62–69; Chen et al, 1991 PNAS 88, p.110), and, more recently, vaccination of mice with HPV-16 E7 elicited a delayed type hypersensitivity response specifically directed against the E7 antigen. Therefore E7 of different papillomaviruses can elicit the appropriate immune response to induce tumour rejection.

TABLE 3

E7 VACCINE

| | WEEKS POST CHALLENGE | | | | | | | | | | | |
|---|---|---|---|---|---|---|---|---|---|---|---|---|
| | 4 | | | 7 | | | 10 | | | 13 | | |
| Lesion Stage | 1 | 2 | 3 | 1 | 2 | 3 | 1 | 2 | 3 | 1 | 2 | 3 |
| Mean number of tumours in vaccinated group | 6.3 [1.2] | 0 | 0 | 5.8 [1.3] | 3.9 [1.3] | 0 | 0.3 [0.3] | 8.7 [0.5] | 0.3 [0.2] | 1.7 [1.2] | 8.1 [0.9] | 0.1 [0.1] |

TABLE 3-continued

| | | | | | | | | | | | | |
|---|---|---|---|---|---|---|---|---|---|---|---|---|
| Mean number of tumours in control group | 3.9 [1.3] | 1.8 [1.5] | 0 | 8 [1.4] | 0.1 [0.1] | 1.1 [1.1] | 2.1 [1.1] | 5.4 [1.6] | 2.5 [1.5] | 1.8 [0.9] | 4.4 [1.7] | 3.1 [1.8] |
| Vaccinated animals with lesions | 11 [100] | 0 | 0 | 8 [72] | 7 [64] | 0 | 1 [9] | 11 [100] | 2 [18] | 5 [45] | 10 [91] | 1 [9] |
| Control animals with lesions | 5 [62] | 3 [37] | 0 | 7 [87] | 1 [12] | 2 [25] | 4 [50] | 6 [75] | 3 [37] | 3 [37] | 5 [62] | 3 [37] |
| Number of lesions in vaccinated animals | 69 [100] | 0 | 0 | 63 [59] | 43 [40] | 0 | 3 [3] | 96 [94] | 3 [3] | 19 [17] | 89 [82] | 1 [0.9] |
| Number of lesions in control animals | 31 [70] | 1 [29] | 10 | 64 [85] | 1 [1] | 10 [14] | 17 [20] | 43 [50] | 25 [29] | 14 [19] | 35 [47] | 25 [34] |

| | WEEKS POST CHALLENGE | | | | | | | | | | | |
|---|---|---|---|---|---|---|---|---|---|---|---|---|
| | 17 | | | 21 | | | 25 | | | 29 | | |
| Lesion Stage | 1 | 2 | 3 | 1 | 2 | 3 | 1 | 2 | 3 | 1 | 2 | 3 |
| Mean number of tumours in vaccinated group | 2 [1.3] | 5 [1.1] | 1.2 [0.9] | 2.5 [1.1] | 2.6 [1.0] | 1 [0.7] | 0.3 [0.2] | 3.8 [1.1] | 0.2 [0.1] | 1.1 [0.5] | 2.6 [0.7] | 0.3 [0.2] |
| Mean number of tumours in control group | 1.8 [0.9] | 3 [1.1] | 3.8 [1.8] | 2 [1.1] | 2.3 [1.1] | 3.5 [1.6] | 0 | 3.5 [1.3] | 2.6 [1.6] | 0.8 [0.4] | 1.3 [0.7] | 0.5 [0.3] |
| Vaccinated animals with lesions | 3 [27] | 9 [82] | 2 [18] | 5 [45] | 7 [64] | 3 [27] | 2 [18] | 9 [82] | 2 [18] | 4 [36] | 8 [72] | 2 [18] |
| Control animals with lesions | 4 [50] | 5 [62] | 3 [37] | 4 [50] | 4 [50] | 4 [50] | 0 | 5 [62] | 4 [50] | 3 [37] | 3 [37] | 3 [37] |
| Number of lesions in vaccinated animals | 22 [24] | 55 [61] | 13 [14] | 27 [40] | 29 [43] | 11 [16] | 3 [6] | 42 [89] | 2 [4] | 12 [27] | 29 [66] | 3 [7] |
| Number of lesions in control animals | 14 [21] | 22 [33] | 30 [45] | 16 [26] | 18 [29] | 28 [45] | 0 | 28 [56] | 22 [44] | 6 [30] | 10 [50] | 4 [20] | a: stage 1, plaque; stage 2, papillomas <2 mm; stage 3, papillomas >2 mm
b: mean number of tumours in a group; SEM in parentheses
c: number of animals with lesions in a group; percentages in parentheses
d: total number of lesions in a group; percentages in parentheses

TABLE 4

| | E7 + L2 and L2 Vaccines weeks post challenge | | | | | | | | |
|---|---|---|---|---|---|---|---|---|---|
| Lesion | 4 | | | 7 | | | 11 | | |
| stage | 1 | 2 | 3 | 1 | 2 | 3 | 1 | 2 | 3 |
| Animal number | | | | | | | | | |
| GROUP 1 (E7 + L2) | | | | | | | | | |
| 1 | 2 | — | — | — | — | — | — | — | — |
| 2 | 1 | — | — | — | — | — | — | — | — |
| 3 | — | — | — | 4 | 3 | — | 1 | 6 | — |
| 4–15 | — | — | — | — | — | — | — | — | — |
| GROUP 2 (L2) | | | | | | | | | |
| 16–26 | — | — | — | — | — | — | — | — | — |
| 27 | — | — | — | 1 | — | — | 5 | 1 | — |
| 28–30 | — | — | — | — | — | — | — | — | — |
| GROUP 3 (control) | | | | | | | | | |
| 31 | 5 | — | — | — | 6 | — | 5 | 1 | — |
| 32 | 1 | 12 | — | 6 | 6 | — | — | 5 | 8 |
| 33 | 5 | — | — | 2 | 8 | — | 3 | 7 | — |
| 34 | 6 | — | — | 2 | 7 | — | 2 | 6 | 4 |
| 35 | — | — | — | — | — | — | — | — | — |
| 36 | — | — | — | — | — | — | 1 | — | — |
| 37 | 11 | — | — | — | 13 | — | 1 | 6 | 4 |
| 38 | — | — | — | — | — | — | — | — | — |
| 39 | ne | — | — | 3 | 2 | — | — | 9 | — |
| 40 | 7 | — | — | 4 | 8 | — | 2 | 9 | 1 |
| 41 | 7 | — | — | 2 | 9 | — | — | 6 | — |
| 42 | ne | — | — | 2 | 5 | — | 1 | 3 | 4 |
| 43 | ne | — | — | 3 | — | — | — | 3 | — |
| 44 | ne | — | — | — | 11 | — | — | 10 | — |
| 45 | ne | — | — | — | 1 | — | 3 | — | — |
| 46 | — | — | — | — | — | — | — | — | — |
| 47 | ne | — | — | 5 | 7 | — | 1 | 8 | — | ne = not examined: numbers represent lesions at each stage; lesion stages as in Table 2. —, no lesions.

We claim:

1. A method of lessening the occurrence and severity of lesions or tumors caused by papillomavirus infection, comprising administering to a mammal post-infection with papillomavirus:

(i) a PV L2 protein or fragment thereof effective to provide a protective effect to lessen the occurrence and severity of lesions or tumors caused by PV infection and an aluminum compound; or (ii) a bovine papillomavirus (BPV) L2 protein or a fragment thereof effective to provide a protective effect to lessen the occurrence and severity of lesions or tumors caused by BPV infection and an aluminum compound; or (iii) a BPV-4 L2 protein or fragment thereof effective to provide a protective effect to lessen the occurrence and severity of lesions or tumors caused by BPV infection and an aluminum compound; or (iv) a BPV-4 protein or fragment thereof effective to provide a protective effect to lessen the occurrence and severity of lesions or tumors caused by BPV infection and an aluminum compound.

2. The method according to claim 1 which comprises administering PV L2 protein or a fragment thereof effective to provide a protective effect to lessen the occurrence and severity of lesions or tumors caused by papillomavirus infection, and an aluminum compound.

3. The method according to claim 2 wherein said PV is BPV.

4. The method according to claim 2 wherein said PV is BPV-4.

5. The method according to claim 1 wherein the papillomavirus protein or fragment thereof effective to provide a protective effect to lessen the occurrence and severity of lesions or tumors caused by papillomavirus infection is in the form of a fusion protein with a different co-protein.

6. The method according to claim 5 wherein the co-protein is GST.

7. The method according to claim 1 wherein the papillomavirus protein or fragment thereof effective to provide a protective effect to lessen the occurrence and severity of lesions or tumors caused by papillomavirus infection is produced by recombinant DNA techniques.

* * * * *